United States Patent [19]

Tsao et al.

[11] Patent Number: 5,918,609
[45] Date of Patent: Jul. 6, 1999

[54] PARTICULATE MODIFIED ELASTOMERIC FLOSSES

[75] Inventors: Belinda L. Tsao, Los Altos Hill; Alex Angell-Atchison, San Francisco; Pranav Desai, Anaheim Hills; Pascal Destandau, San Francisco; Pritpal Singh, Newark, all of Calif.

[73] Assignee: Gillette Canada Inc., Kirkland, Canada

[21] Appl. No.: 08/738,982

[22] Filed: Oct. 24, 1996

[51] Int. Cl.$^6$ ..................................................... A61C 15/00
[52] U.S. Cl. .......................... 132/321; 132/200; 132/323
[58] Field of Search .................................... 132/321, 323, 132/325, 326, 327, 328, 329, 200

[56] References Cited

U.S. PATENT DOCUMENTS

| | | | |
|---|---|---|---|
| 1,526,039 | 2/1925 | Arkell et al. | |
| 2,369,847 | 2/1945 | Olsen et al. | 98/140 |
| 2,667,443 | 1/1954 | Ashton | 167/93 |
| 2,700,636 | 1/1955 | Ashton | 167/93 |
| 2,748,781 | 6/1956 | Collat | 132/93 |
| 2,886,440 | 5/1959 | Kramer et al. | 99/135 |
| 2,886,445 | 5/1959 | Rosenthal et al. | 99/135 |
| 2,886,446 | 5/1959 | Kramer et al. | 99/135 |
| 2,886,449 | 5/1959 | Rosenthal et al. | 99/135 |
| 3,699,979 | 10/1972 | Muhler et al. | 132/89 |
| 3,771,536 | 11/1973 | Dragan | 132/89 |
| 3,800,812 | 4/1974 | Jaffe | 132/89 |
| 3,830,246 | 8/1974 | Gillings | 132/89 |
| 3,838,702 | 10/1974 | Standish et al. | 132/89 |
| 3,860,013 | 1/1975 | Czapor | 132/91 |
| 3,897,795 | 8/1975 | Engel | 132/89 |
| 3,943,949 | 3/1976 | Ashton et al. | 132/321 |
| 3,991,766 | 11/1976 | Schmitt et al. | 128/335 |
| 4,033,365 | 7/1977 | Klepak et al. | 132/89 |
| 4,175,326 | 11/1979 | Goodson | 433/80 |
| 4,276,312 | 6/1981 | Merritt | 426/96 |
| 4,360,514 | 11/1982 | Buck | 434/56 |
| 4,362,712 | 12/1982 | Buck | 424/49 |
| 4,403,089 | 9/1983 | Buck | 528/247 |
| 4,414,990 | 11/1983 | Yost | 132/91 |
| 4,528,226 | 7/1985 | Sweeny | 428/40 |
| 4,627,975 | 12/1986 | Lynch | 424/49 |
| 4,678,814 | 7/1987 | Rembaum | 522/175 |
| 4,764,377 | 8/1988 | Goodson | 424/435 |
| 4,780,320 | 10/1988 | Bakar | 424/443 |
| 4,828,955 | 5/1989 | Kasai et al. | 430/111 |
| 4,892,736 | 1/1990 | Goodson | 424/435 |
| 4,904,479 | 2/1990 | Illum | 424/490 |
| 4,911,927 | 3/1990 | Hill et al. | 424/443 |
| 4,952,392 | 8/1990 | Thame | 424/58 |
| 4,959,220 | 9/1990 | Yamamoto et al. | 434/435 |
| 4,974,614 | 12/1990 | Selker | 132/321 |
| 5,033,488 | 7/1991 | Curtis et al. | 132/321 |
| 5,037,818 | 8/1991 | Sime | 514/183 |
| 5,076,300 | 12/1991 | Mayfield | 132/321 |
| 5,353,820 | 10/1994 | Suhonen et al. | 132/321 |
| 5,433,226 | 7/1995 | Burch | 132/321 |
| 5,479,952 | 1/1996 | Zachariades et al. | 132/321 |
| 5,508,334 | 4/1996 | Chen | 132/321 |
| 5,565,206 | 10/1996 | Spencer | 132/321 |
| 5,697,390 | 12/1997 | Garrison et al. | 132/321 |

FOREIGN PATENT DOCUMENTS 0 292 673 A2  11/1988  European Pat. Off. .

OTHER PUBLICATIONS

"Kraton Thermoplastic Rubbers in oil gels," Technical Bulletin Shell Chemical Company, Apr. 1989, pp. 3–11.
C. Chiang, "Sample Batch for Panel Evaluation," Applied Elastomerics, Inc. Aug. 25, 1994, 11 pgs.
Chi–Tang Ho et al. "Flavor Technology, Physical Chemistry, Modification and Process," ACS Symposium Series, Aug. 21–25, 1994, 10 pgs.

*Primary Examiner*—Gene Mancene
*Assistant Examiner*—Pedro Philogene
*Attorney, Agent, or Firm*—Fish & Richardson P.C.

[57] ABSTRACT

Elastomeric polymeric flosses comprising particulate modification agents stably associated with the surface thereof, as well as methods for their fabrication, are provided. In the subject flosses, particulate modification agents are either adsorbed to the surface of the floss or embedded in the surface of the floss. To fabricate the subject flosses, unmodified elastomeric flosses are contacted with particulate modification agents under conditions which provide for the stable association of the particles with the floss surface, where the floss surface may be softened to promote embedding of the particulate modification agents in the surface of the floss.

16 Claims, 3 Drawing Sheets

*Cross-section of floss showing microsponge physically embedded on the surface of the filament*

Cross-section of floss showing microsponge physically embedded on the surface of the filament Cross-section of floss showing clumps of spray-dried particles adhered to the surface of the filament

*Micrograph of the length of floss dusted with spray-dried powder*

FIG. 3

PARTICULATE MODIFIED ELASTOMERIC FLOSSES

FIELD OF THE INVENTION

The field of the invention is dental floss.

BACKGROUND OF THE INVENTION

Tooth decay and dental disease can be caused by bacterial action resulting from plaque formation around the teeth and/or the entrapment of food particles in interstices between teeth. Removal of plaque and entrapped food particles reduces the incidence of caries, gingivitis, and mouth odors as well as generally improving oral hygiene. Conventional brushing has been found to be inadequate for removing all entrapped food particles and plaque. Therefore, to supplement brushing, dental flosses and tapes are often employed.

Traditional flosses have been fabricated from yarns of natural fibers, such as linen, silk, and cotton as well as various synthetic fibers, such as nylon. In order to improve the ability of floss to be inserted into the interstices between teeth, flosses have been coated with a variety of materials, such as waxes. In addition to improving floss lubricity during use, wax coatings have also been used as carrier materials for floss modification agents, such as flavoring oils, medicaments, texturants and the like.

Traditional flosses are not entirely satisfactory for a number of reasons, including their limited ability to assume thinner or thicker shapes to accommodate different sized spaces between teeth, their tendency to fray under conditions of normal use, and their lack of comfort for the user.

In order to overcome these problems with traditional flosses, efforts have been made to prepare 'new generation' flosses of polymeric elastomeric materials. Among other advantages, flosses prepared from such materials have the potential to assume a number of different thicknesses depending on the stress to which they are subjected, and therefor can be readily tailored to a user's individual needs.

Despite the potential of such 'new generation' flosses, problems have been encountered in the modification of such flosses with flavorants or other modification agents. Traditional wax carrier materials do not work with elastomeric flosses as the wax is not itself sufficiently elastic and therefore tends to crack under stress. Other problems found when attempts are made to modify elastomeric flosses with traditional flavor oils include inefficient use of such flavor oils, solvation of the floss material by the flavor oil, and the like.

Accordingly, there is interest in the development of new methods of modifying polymeric elastomeric floss materials. Ideally such methods should be relatively simple to perform, adaptable to large scale production needs and provide for efficient use of the modification agent.

Relevant Literature

U.S. Pat. Nos.: 2,677,443; 2,748,781; 3,699,979; 3,771,536; 3,800,812; 3,830,246; 3,897,795; 3,943,949; 4,033,365; 4,414,990; 4,911,927; 4,974,614; 5,076,300; 5,353,820; 5,433,226; as well as EP 0 292,673 all describe floss designs.

U.S. Pat. Nos.: 1,526,039; 2,369,847; 2,700,636; 2,886,440; 2,886,445; 2,886,446; 2,886,449; 3,991,766; 4,276,312; 4,528,226; 4,678,814; 4,828,955 describe different methods of flavoring polymeric materials, as well as the production of encapsulated agents such as flavoring agents. The preparation of flavor products is also reviewed in "Flavor Technology," ACS Symposium Series 610 (Ho, Tan & Tong eds., 1995).

SUMMARY OF THE INVENTION

Elastomeric flosses comprising particulate modification agents stably associated with their surface, as well as methods for their fabrication, are provided. The particulate modification agents may be either embedded in, or adsorbed on, the surface of the floss, where such agents may be flavorants, medicaments, texturants and the like. In preparing the subject flosses, the surface of the to be modified floss is contacted with the particulate modification agents under conditions sufficient to provide for the stable association. Thus, with flosses having sufficiently tacky surfaces, it is sufficient to contact the floss with the modification agent with no further action being necessary. Alternatively, the surface of the floss may be softened, molten or quasi-molten prior to contact with the particulate modification agents, such that the particulate modification agents become embedded in the floss surface.

The file of this patent contains at least one photograph executed in color. Copies of this patent with color photographs will be provided by the Patent and Trademark Office upon request and payment of the necessary fee.

BRIEF DESCRIPTION OF THE FIGURES

FIG. 3 is a photograph of the length of a floss dusted with spray-dried powder according to the subject invention.

DESCRIPTION OF THE SPECIFIC EMBODIMENTS

Figure 1:
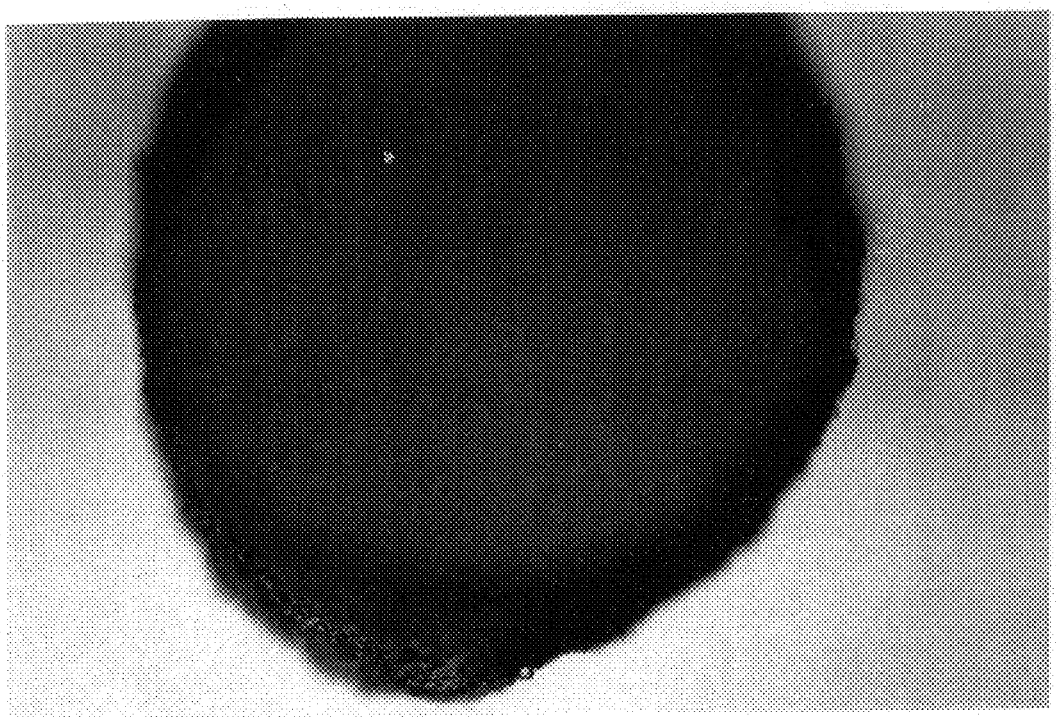
FIG. 1 is a photograph of a cross section of a floss according to the subject invention showing microsponge physically embedded on the surface of the floss filament.

Elastomeric flosses having particulate modification agents stably associated with their surface, as well as methods for their fabrication, are provided. In the subject flosses, the particulate modification agents may be either embedded in, or adsorbed to, the surface of the floss. In fabrication of the subject flosses, the floss surface is contacted with the particulate modification agent, where the surface may be in a softened or quasi-molten or molten state so that the particulate modification agents become embedded in the surface. In further describing the subject invention, first the modified flosses themselves will be discussed in greater detail followed by a more comprehensive description of how the subject flosses are prepared.

Before the subject flosses and methods for their preparation are further described, it is to be understood that the invention is not limited to the particular embodiments or extrusion methodologies described. Such flosses and methodologies may, of course, vary. It is also to be understood that the terminology used herein is for the purpose of describing particular embodiments only, and is not intended to be limiting. Instead, the scope of the present invention will be established only by the appended claims.

It must be noted that as used in this specification and the appended claims, the singular forms "a", "an" and "the" include plural reference unless the context clearly dictates otherwise. Thus, for example, reference to "a polymer" includes mixtures of different polymers. Unless defined otherwise all technical and scientific terms used herein have the same meaning as commonly understood to one of ordinary skill in the art to which this invention belongs. Although any methods and materials similar or equivalent to those described herein can be used in the practice or testing of the present invention, the preferred methods and materials are now described. All publications mentioned herein are incorporated herein by reference.

The flosses according to the subject invention will comprise particulate modification agents stably associated with the surface of the flosses. The flosses may be fabricated from any thermoplastic elastomeric material, where the thermoplastic elastomeric material is usually extrudable. Materials of interest include synthetic rubbers and plastics, such as materials based on polyurethanes, polystyrenes, polyamides, polyesters, polyolefins and the like, where a particularly preferred type of flosses that may be modified according to the subject invention are the gel flosses described in application Ser. No. 08/699,891 filed on Aug. 15, 1996, the disclosure of which is herein incorporated by reference.

In the gel flosses described in the 08/699,891 application, both the core and gel materials employed in the subject flosses will be thermoplastic elastomeric materials. The thermoplastic materials used for the gel and core components of the floss of this particular gel floss preferably have an elasticity above 200% and preferably above 300%. The melting points of the core and gel thermoplastic elastomeric polymers will not vary by more than about 50° F.

The core components of these preferred gel flosses provide the requisite elasticity and strength characteristics to the flosses. The core component will be fabricated from a thermoplastic elastomeric polymeric material capable of being extruded into chords, threads, rods, filaments and the like (hereinafter collectively referred to as "fibers"). Suitable core materials will have an overall tensile strength, as measured by ASTM method D412, of at least 500 psi, and usually at least 2000 psi. The elasticity of the core materials, as measured by ASTM D412 will be at least 200% and usually at least 400%.

The core elastomeric material will usually be a blend of at least two different polymeric components, where at least one of the polymeric components is the base component and at least one of the polymeric components provides for strong adhesion between the core and gel components of the floss, e.g. is chemically similar to polymeric components of the gel portion of the floss. Polymers finding use in the core component include both addition and condensation polymers. Polymeric materials finding use may be homo- or copolymers, where the copolymers may be polymerized from 2 to 6 different monomeric units. Of interest as homo- and copolymers are polystyrenes, polyethers block amides, polyurethanes, polyesters, polyolefins, caprylactam based polyurethanes, and the like.

Specific core thermoplastic elastomeric polymers or components of interest include: styrenic-based elastomeric copolymers. Examples of styrenic based elastomeric copolymers include SEBS, available from Shell under the tradename KRATON®, and from Consolidated Polymer Technologies (CPT) under the tradename C-Flex; SEPS (Styrene-Ethylene-Propylene-Styrene), available from M. A. Hanna; and SEP/EBS (Styrene-Propylene-Butylene-Styrene), and available SEPS available from Kuraray Co. Specific non-styrenic polymers finding use include: (a) polyether block amides such as those available under the tradename PEBAX® from Elf Atochem; (b) polyurethane-based materials (thermoplastic urethanes (TPUs)), such as Tecoflex and Tecothane, both available from Thermedics Inc., Pellathan, available from Dow Chemical, and Elastollan, available from BASF; (c) polyester-based thermoplastic elastomers, such as Hytrel available from DuPont; (d) polyolefin-based thermoplastic elastomers, such as SARLINK available from DSM Corp. and SANTOPRENE available from AES Corp.; and (e) caprylactam-based polyurethanes.

Particularly preferred core component materials include: a blended material of TPU/SEPS commercially available from M. A. Hanna as HTE 2203, and a one:one blend of PEBAX MX1205/KRATON FG1901.

The gel component of the subject gel flosses imparts softness to the flosses and, therefore, makes the subject flosses comfortable to use. The gel material will also have a tear resistance, as measured by the ASTM die "C" tear test, ASTM No. D412 run at 23° C. and 20 in./min, of at least 20 pounds per linear inch (pli), or higher, where in some instances the gel material will not tear at maximum elongation under stress. The subject flosses will have a shore hardness of no more than about 10 A, usually no more than about 5 A, where the shore hardness will generally be at least about 0 A, and more usually at least about 2 A.

The gel component will comprise at least one styrenic based elastomeric copolymer, in combination with at least one oil plasticizers or flexibilizers, such as a mineral oil, silicone oil, napthenic oil and the like. The ratio of elastomeric copolymer to oil in the gels will typically range from about 100 parts resin to at least 100 parts oil, usually at least 400 parts oil, where the ratio of the two components may be 100 parts resin to as much as 2000 parts oil.

Styrenic based copolymers will generally be copolymers of styrene and one or more monomers, usually olefinic monomers, where illustrative olefinic monomers include ethylene, propylene, butylene and the like. Specific styrenic based copolymers of interest include SEPS (styrene-ethylene-propylene-styrene) copolymers, such as those sold under the trade names Septon 2006, Septon 4055, and the like.

Oils of interest for use in the subject gel components include both high and low viscosity oils, where by low viscosity oils is meant that the oil has a saybolt, a viscosity unit (SVU) measured by ASTM D2161 ranging from about 90 to 200 cps, usually from about 60 to 120 cps, and by high viscosity oil is meant a SVU that is 400 to 500 cps, usually at least about 350 cps, with medium viscosity oils being those oils having viscosities falling between the viscosities of the high and low viscosity oils, as defined above. Specific silicone oils of interest include those sold under the trade names Sentry Dimethicone NF 350, and the like. Mineral oils of interest include those sold under the trade names Duoprine 90, Kaydol, Hydrobrite, Britol, and the like.

In addition to the oil and resin, as described above, the gel component of the subject flosses may be formulated to comprise one or more additional processing aids. Processing aids which may be present in the gel formulation include: extenders, such as oils, waxes, resins, asphalts and the like; low molecular weight polyolefins, e.g. polyethylene, and the like; adhesives, e.g. EVA; tackifiers, e.g. alpha methyl/vinyl styrene,; etc. When present, such additional processing aids will make up from about 5 to 70% by weight of the gel material.

Preferred specific gel material formulations for use in the preferred gel flosses include the styrenic-based copolymers such as those available from GLS Corporation (Cary, Ill.), such as LC 115-035B, LC115-101B , based on KRATON G-1651; SEPS gels, such as XL0141-8, -21, -22, -23, -24, -25, -26, -27, -30, -32, -34, -35, described in greater detail in the experimental section below, and the like. Specific gel material formulations which provide for gel flosses with sufficiently tacky surfaces to provide for stable attachment of particulated modification agents to the surface of the floss, as described above, include XL0141-21, -22, -25, -30, -32, -34, -35 and the like, as well as those gel formulations described U.S. Pat. No. 5,508,334, entitled Thermoplastic Elastomeric Gelatinous Compositions and Articles, the disclosure of which is herein incorporated by reference.

The particulate modification agents stably associated with the surface of the elastomeric polymeric material in the subject flosses may be texturants, medicaments, flavorants, pigments, and the like. The particles may range in size from about 10 $\mu$ to about 300 $\mu$, where the particulate size may vary depending on the particular type of particulate modification agent, e.g. for flavorant particles the size will usually range from about 20 to 100 $\mu$ while for texturante particles the size may range from 50 to 300 $\mu$, where the shape of the particles may be any of a number of different shapes, such as spherical, square, cylindrical, irregular and the like, the shape being dependent primarily on the particulate manufacturing method employed.

Texturant particulate modification agents include calcium carbonate, talc, silica, dicalcium phosphate, tetra sodium pyrophosphate, tetra potassium pyrophosphate, sodium bicarbonate, zirconium silicate, calcium pyrophosphate, anhydrous calcium hydrogen phosphate, calcium hydrogen phosphate dihydrate, insoluble metaphosphate, alumina, tin dioxide and the like, as described in U.S. Pat. Nos. 4,911,927 & 3,699,979, the disclosures of which are herein incorporated by reference. Also, other texturent particulate modification agents which are compatible with the gel material may be used, these include polyolefins, kraton-based polymers and the like.

Medicament particulate modification agents of interest include particulate forms of agents known to retard tooth decay, such as particulate sources of fluoride ions, including particulate forms of fluoride salts, such as sodium fluoride, stannous fluoride, titanium fluoride, sodium monofluorophosphate, amine fluoride, and the like, as described in U.S. Pat. No. 4,414,990, the disclosure of which is herein incorporated by reference. Also, other suitable medicament particulate modification agents include Triclosan chlorehexidiane, calcium pyrophosphate and the like.

Of particular interest as particulate modification agents in the subject flosses are flavorant particulate modification agents. Flavorant particle technology is well known in the art and reviewed in "Flavor Technology, Physical Chemistry, Modification and Process," ACS Symposium Series 610 (Ho et al., Eds 1995), as well as U.S. Pat. No. 4,276,312, the disclosures of which are herein incorporated by reference. Flavorant particles of interest in the subject invention will include both powder adsorbed and microencapsulated particles, where microencapsulated particles of particular interest include those prepared by spray drying, spray chilling, extrusion, molecular inclusion (cyclodextrin), coacervation and co-crystallization.

One class of spray dried particles of particular interest include those comprising a flavor oil in combination with either water insoluble or water soluble matrices. Spray dried particles comprising flavorant oil in combination with a water-soluble matrix include those described in U.S. Pat. No. 3,943,949, the disclosure of which is herein incorporated by reference. Suitable water soluble matrix materials for use in such spray dried particles include gums, such as gum acacia, gum arabic, gum tragacenth and the like; starches, such as corn starch; dextrins and the like. Suitable flavors include peppermint, spearmint, wintergreen, cassia, cinnamon, cherry, strawberry, lime and the like.

The particular type of flavor particle selected will depend in part on the nature of the elastomeric floss to be modified as well as the method of modification, e.g. by surface penetration or surface adsorption. For example, with particles that embedded in the surface of the elastomeric floss, the particles should be inert with respect to the elastomeric material, such that they do not react chemically react with the material or physically degrade the material. Furthermore, where the particles embedded in the surface of the floss prior to quenching in an aqueous quenching means, as described in greater detail below, the particles should be encapsulate in a non-water soluble matrix material. Similarly, where the particles are to be adsorbed to the surface of the floss which is sufficiently tacky by virtue of an oil blooming to its surface, the particles should comprise an encapsulation material that is wettable by, yet insoluble in, the oil, as described in greater detail below.

By having a surface modified to comprise the particulate modification agents, what is meant is that the particulate modification agents are stably associated with the surface of the gel floss, where stably associated means that the particulate modification agents do not readily separate from the surface of the floss therefor, after manufacturing and packaging process. In other words, what is meant by stably associated is that a substantial portion of the particles are not removed from the surface of the floss after manufacturing and packaging process and allow for sufficient flavor upon use, where by "substantial portion" is meant more than about 50 number percent of the originally associated particles, such that following subjection to stressful conditions which approximate the conditions of normal use, at least about 50 number percent of the originally associated particles remain associated with the floss surface.

As mentioned above, in the subject flosses, the particles may be adsorbed to the surface or actually embedded in the surface of the floss material, such that only a portion of the particle is present above the surface of the material. In embodiments where the particles are embedded in the surface of the floss, the particles will extend to a depth sufficient to provide for the stable association.

In preparing the subject flosses, the elastomeric polymeric flosses will generally be prepared using extrusion methods as are known in the art, with the preferred gel flosses referenced above being more specifically prepared according to the method disclosed in application Ser. No. 08/699,891, the disclosure of which is herein incorporated by reference. Briefly, in this method a core and gel material of these gel flosses are coextruded through a multicomponent die assembly, where the coextrudate is then quenched to produce the floss.

In the method according to the subject invention, the floss material will be contacted with the particles under conditions sufficient to stably associate the particles with the surface of the gel. Depending on the nature of the floss material and that of the particles, the surface of the material may or may not be in a softened or quasi-molten state during contact.

For those formulations of gel floss in which the surface is sufficiently tacky to provide for sufficient adherence of the particles to the surface, the particles will be contacted with the surface using any convenient means, including dusting, modified fluidized bed, metered dispensing, and the like. Generally, the temperature at which contact takes place will be room temperature. By sufficiently tacky is meant that when 2 pieces of floss made with a sufficiently tacky material are placed in contact with each other, the two pieces will remain stuck together unless some force is applied in order to peel them apart. Illustrative floss materials which are suitably tacky for modification by this method include XL0141-21, 22, 25, 30, 32, 34 and 35, as further described in the Experimental section, supra.

In the embodiment of the subject invention where particles are adsorbed to the surface of sufficiently tacky elastomeric flosses which are tacky because of oil on the surface of the material, the particles will preferably be spray dried microencapsulated particles, where the particles are microencapsulated in a material which is sufficiently wetted by, yet insoluble in, the oil present on the surface of the material. Any encapsulation material which is sufficiently wetted by the oil but insoluble in the oil may be used, where illustrative materials include starches, polyvinylpyrrolidone, cyclodextrins and the like.

The floss can be subjected to an excess of particulates to ensure saturation of adsorbed particles on the tacky floss surface. The amount of particulate modification agent which is applied to the surface of the tacky elastomeric floss at saturation will typically range from 0.2 to 2.0 weight % of the elastomer and preferably from about 0.5 to 1.5 weight % of the elastomer. The conditions under which the tacky elastomeric floss is contacted with an excess of particulate modification agents, usually microencapsulated particles, in excess was removed by conventional methods (e.g., air blowing), should be such that, at least 50 number % of the originally contacted particles remain associated with the surface of the floss after downstream processing. After application of the particles, the surface of the floss will no longer be tacky, as defined above. Alternatively, the application of the particles to the surface can be controlled to deliver only the desired amount.

Instead of adsorbing particles to the surface of the floss, the floss material may be contacted with the particles under conditions where the floss material at least at the surface of the floss is in sufficiently softened molten, quasi-molten or semi-molten state such that the particles contacted with the surface become embedded in the surface of the floss upon contact. The requisite softness for this method can be determined empirically, based on factors such as the nature of the particles, the nature of the floss material and the like, where the material will be determined to be sufficiently softened when, following contact of the particles with the surface and subsequent application of stress to the floss, at least 75 number % of the originally associate particles will be remain associated with the surface of the floss.

To achieve embedding of the particles in the surface of the floss, the temperature of the elastomeric material at the surface of the floss will be chosen to provide for the necessary softness or quasi-molten qualities, as described above. To provide for the requisite embedding of the particles in the floss surface, upon contact the particles will have sufficient momentum to ensure that they embed in the softened or quasi-molten surface of the floss, where sufficient momentum will depend on the mass and velocity of the particles in view of the nature of the material. Any convenient contacting means capable of provided for particle penetration of the surface may be employed, where such means include spraying, dusting, and the like.

Following contact of the particles with the surface of the gel and subsequent penetration of the particles below the surface of the floss, the floss will be cooled to embed the particles in the floss, producing a floss with stably associated particles on its surface. The temperature of the coolant (e.g., air or water) to which the floss is quenched will generally range from about 30 to 80° F. The floss may be cooled using any convenient means, including quenching in cool water, blowing with chilled air, and the like.

The subject flosses may be contacted with the particles after being extruded but prior to quenching. In such embodiments where quenching is accomplished using aqueous means, e.g. a cool water bath, the particles should be non-water soluble particles, so that they are not removed from the surface during quenching. Instead of contacting the floss prior to quenching, the quenched floss may be reheated to a temperature sufficient to soften the surface, as described above, and then contacted with the particles. Where the particles are contacted with a reheated gel floss post-quench, following contact the floss material will again be cooled to stably secure the particles to the surface of the gel floss.

The following examples are offered by way of illustration and not by way of limitation. The following examples are put forth so as to provide those of ordinary skill in the art with a complete disclosure and description of how to make the monofilament flosses and carry out the extrusion methodology of the invention, and are not intended to limit the scope of what the inventors regard as their invention. Efforts have been made to ensure accuracy with respect to numbers used (e.g., amounts, temperatures, etc.) but some experimental errors in deviation should be accounted for.

EXPERIMENTAL

A. Equipment Set-Up For Gel Floss Fabrication

The following description of an equipment set-up and manufacturing procedure is representative of that used to create the gel flosses described in greater detail below. Two 1.25-inch diameter extruders were connected to a two-component extrusion die with metering pumps on each screw operating to deliver the flowrate of material to the die to form a floss having a ratio of 50:50 core material:gel material. The bi-component extrusion die included a metering plate, a distributing plate, and a spinneret/die. Operating temperatures of the equipment and molten materials were recorded at various stages before leaving the die. After being coextruded through the extrusion die according to standard methods, the extrudate was processed with a downstream filament spinning set-up to produce floss. The downstream set-up included a quenching water bath, tension-controlled rollers and a winder.

TABLE 1

| Material | XLO 141 -8 (%) | XLO 141 -21 (%) | XLO 141 -22 (%) | XLO 141 -23 (%) | XLO 141 -24 (%) | XLO 141 -25 (%) | XLO 141 -26 (%) | XLO 141 -27 (%) | XLO 141 -30 (%) | XLO 141 -31 (%) | XLO 141 -32 (%) | XLO 141 -34 (%) | XLO 141 -35 (%) |
|---|---|---|---|---|---|---|---|---|---|---|---|---|---|
| Septon 4055 (SEPS) | 16.8 | 16.63 | 16.44 | 22.03 | 16.44 | 24.90 | 16.6 | 11.07 | 15.97 | 15.48 | 15.97 | 15.97 | 15.97 |
| Britol 50T (High Mol. Wt. Mineral Oil) | 80.0 | | | | | | | | | | | | |
| Irganox 1010 (antiox.) | 0.1 | 0.1 | 0.1 | 0.1 | 0.1 | 0.1 | 0.1 | 0.1 | 0.1 | 0.10 | 0.10 | 0.1 | 0.1 |

TABLE 1-continued

| Material | XLO 141 -8 (%) | XLO 141 -21 (%) | XLO 141 -22 (%) | XLO 141 -23 (%) | XLO 141 -24 (%) | XLO 141 -25 (%) | XLO 141 -26 (%) | XLO 141 -27 (%) | XLO 141 -30 (%) | XLO 141 -31 (%) | XLO 141 -32 (%) | XLO 141 -34 (%) | XLO 141 -35 (%) |
|---|---|---|---|---|---|---|---|---|---|---|---|---|---|
| Irgafos 168 (antiox.) | 0.1 | 0.1 | 0.1 | 0.1 | 0.1 | 0.1 | 0.1 | 0.1 | 0.1 | 0.10 | 0.10 | 0.1 | 0.1 |
| Engage EG 8200 | | | | | | | | | 2.97 | 5.94 | | | |
| Exxon PP 3505 G | | | | | | | | | | | | 2.97 | 2.97 |
| Affinity SM 1300 | | | | | | | | | | | 2.97 | | |
| Affinity PL 1880 (modifier: low MWPE) | 3.0 | 2.97 | | | | | | | | | | | |
| Sentry Dimethacone NF 350 | | | | 14.85 | | | | | | | | | |
| Duoprime 90 (mix) | | | | | 41.08 | 37.35 | 41.5 | 44.27 | | | | | |
| Duoprime 90 (inject) | | | | | 41.08 | 37.35 | 41.5 | 44.27 | | | | | |
| Kemamide E (used as an antiox.) | | | .20 | 0.20 | 0.20 | 0.2 | 0.2 | 0.2 | | | | | |
| Kaydol (blend) | | | | | | | | | | | | | 39.93 |
| Kemira OR 470 | | 1.00 | 1.00 | 1.00 | 1.00 | | | | 1.00 | 1.00 | 1.00 | | |
| Kaydol (inject) | | | | | | | | | | | | | 39.93 |
| Hydrobrite 200 (mix) | | 39.60 | 41.08 | 30.86 | | | | | 39.93 | 38.69 | 39.93 | | |
| Hydrobrite 200 (side inject) | | 39.60 | 41.08 | 30.86 | | | | | 39.93 | 38.69 | 39.93 | | |

TABLE 2

| Property | -21 | -22 | -23 | -24 | -30 | -32 | -34 | -35 |
|---|---|---|---|---|---|---|---|---|
| Elongation (%) | 1000 | 1070 | 1000 | 1000 | 1170 | 1110 | 1114 | 1100 |
| 50% modulus (psi) | 15 | 4 | | 5 | 3 | 6 | 5 | 1 |
| 100% modulus (psi) | 22 | 7 | | 6 | 7 | 8 | 8 | 4 |
| 200% modulus (psi) | 35 | 10 | | 10 | 10 | 13 | 12 | 7 |
| 300% modulus (psi) | 49 | 15 | | 13 | 17 | 20 | 20 | 15 |
| Tensile (psi) | 184 | 67 | | 86 | 99 | 132 | 175 | 163 |
| Hardness 1 (A) (shore A) | 11 | 6 | | 6 | 6 | 7 | 6 | 7 |
| Melt Flow Rate 1 (2.16 kg @ 230° C.) | 45.74 | 328.5 | | | 105 | 52.30 | 190 | 170 |
| Melt Flow Rate 2 (2.16 kg @ 150° C.) | 5.5 | 14.7 | | 42 | 11.3 | 3.4 | 96 | 84 |
| Tension Set (100% @ 23° C.) | 3.0 | 1.5 | | 2.3 | 3.5 | 1.8 | 2.0 | 3.5 |
| Compression Set ((22 hrs @ 23° C.) | 7.2 | 4.7 | | 14.0 | | | | |
| Density (g/cm$^3$) | .89 | .88 | | .85 | .88 | .88 | .88 | .88 |
| Tear Resistance (pli) | 33 | | | 26 | 30 | | | |

TABLE 3

| Example No.: | 1 | 2 | 3 | 4 | 5 |
|---|---|---|---|---|---|
| Date of Run | 06/17/96 | 03/07/96 | 02/14/96 | 01/26/96 | 03/07/96 |
| Cross-section | 34 islands/sea + rod; FIG. 6b | 34 islands/sea tape | Core/sheath | Core/sheath tube; FIG. 4c | Multiple Bicomponent Filaments |
| Core | TPU/KRAT. | TPU/KRAT. | Hanna HTE | PEBAX MX1205/ | Hanna |

TABLE 3-continued

| Example No.: | 1 | 2 | 3 | 4 | 5 |
|---|---|---|---|---|---|
| Component | HTE 2203 | HTE 2203 | 1113 (Shore A 66 SBS) | KRATON FG1901 1:1 blend | TPU/KRATON blend HTE 2203 |
| Sheath Comp. | SEPS gel XLO141-8 | GLS G6713 KRATON | GLS LC115-035B | GLS LC 115-035B | GLS KRATON G6713 |
| Ratio (Sheath/Core) | 50/50 | 50/50 | 80/20 | 80/20 | 30/70 |
| Sheath O.D./Core O.D. (in.) | Rod 0.08" O.D. | 0.0065" × 0.372" tape | 0.07"/ 0.032" | 0.060"/ 0.032"; tube 0.020" | — |
| Metering Pumps (size (cc)/speed (rpm)) | 6 cc/5 rpm both | 6 cc/3 rpm both | 1 amp/19.5 rpm for sheath mat'l; no melt pump for core mat'l | 1 amp/19.5 rpm for sheath mat'l; no melt pump for core mat'l | 6 cc/2.4 rpm (sheath) 6 cc/5.6 rpm (core) |
| Temp. of Core mat'l at die exit (° C.) | 201 | 199 | not measured | not measured | 196 |
| Temp. of Sheath mat'l at die exit (° C.) | 205 | 200 | not measured | not measured | 197 |
| Temp. of Spin Head (° C.) | 210 | 203 | 182 | 182 | 203 |
| Winder Speed (mpm) | 20 | Manual wind | 22.3 ft/min | approx 22 ft/min. | hand-wound |
| Fray Test (avg. of 5 runs) | 147+/−8 Blunt | 197 Blunt; 3.2 +/−0.2 Sharp | 24 +/−1 Blunt | 62 +/−10 Blunt | 96 filaments: 32+/−2 cycles (Sharp) 48 filaments: 37+/−3 cycles (Sharp) |
| Tensile strength (kg) | 3.1 +/−0.1 | not measured | | | |
| Comments | | 15 mm × 0.17 mm slot die; vertical extrusion | | | |

E. Modification of Gel Floss Material with Particulate Modification Agents

1. Particulate Modification Agents Contacted to Quenched Elastomeric Floss

A gel floss comprising the XL014 1-21 gel material on its surface was heated using a hot air gun at approximately 100–150° C. until the surface of the material reached a softened, quasi-molten state. The heated surface was then subject to a spray of powder and air using a powder spray device, where the particles were microsponge particles (Advanced Polymer Systems, CA). The floss was then air cooled to room temperature.

The treated floss was examined under a microscope. It was observed that the floss surface had minute particles embedded or sticking to the surface. The treated floss was subject to a high pressure stream of air in an effort to dislodge the particles and determine how stably the particles were associated with the surface of the floss. Upon reexamination of the floss surface, it was observed that the particles had not been dislodged in any significant quantity. A photograph of a cross-sectional view of the floss clearly showing the particles embedded in the floss surface is provided in FIG. 1.

The above experiment was repeated with a number of different particles, with the similar results being obtained for each modified floss.

2. Particulate Modification Agents Contacted With Elastomeric Floss Prior to Quenching A surface modified floss was prepared as described in D above, with the following modifications. Immediately following extrusion of the floss from the die but prior to submersion of the extruded floss in the water bath, the floss was sprayed with a powder of microsponge using a metering dispensing device (Christy Machine Co., Ohio). The cooled floss following submersion in the water bath was observed with a microscope. The surface of the floss was observed to have particles of microsponge embedded in it. The floss was then subjected to stressful handling in an effort to determine how stably associated the particles wore on the surface of the floss. Upon observation, it was found that no significant amount of the particles had been dislodged from the surface of the floss.

3. Adsorption of Particulate Modification Agents to the Surface of Tacky Floss

Figure 2:
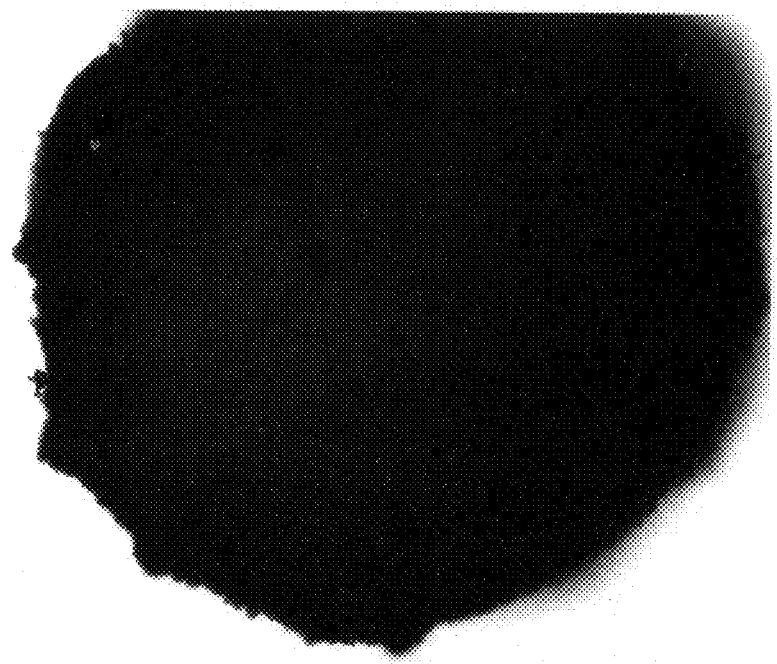
FIG. 2 is a photograph of a cross section of a floss according to the subject invention showing clumps of spray-dried particles adhered to the surface of the floss filament.

A monofilament floss was prepared of the XL-0141-21 gel material described above. Spray dried flavorant particles Quest TP2850SD (Quest International Fragrances Co., NJ) was dusted on the surface of the monofilament and the excess removed by agitation. The dusted particles were observed to be stably associated with the surface of the floss. See FIGS. 2 and 3.

It is evident from the above results and discussion that improved methods of modifying the properties of elastomeric polymeric flosses are provided. With the subject methods, the modification agent is used efficiently as the amount of modification agent employed is only as great as that required to cover the surface of the material. Furthermore, since the modification agent is present on the surface of the floss, and not dispersed throughout the floss material, its effectiveness is enhanced, e.g. where the modification agent is flavorant particle, having the flavorant particle present on the surface of the floss ensures that a sufficient amount of flavor particle comes in contact with the floss user to ensure a satisfactory flavor impact. Finally, the subject methods provides an alternative to methods dependent on the use of carrier materials, such as the conventional application of waxes and flavors, which are ineffective with elastomeric flosses.

Other embodiments are within the claims.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method of producing a gel floss having a surface to which is stably associated flavor particles, said method comprising:

providing said gel floss with a sufficiently tacky surface to provide adherence for stable association of said microparticles thereto;

contacting said surface with said particles;

whereby said gel floss having flavor particles stably associated with said surface is produced.

2. The method according to claim 1, wherein said gel floss comprises a core component encased in a gel component, wherein said gel component comprises a styrenic based resin in combination with an oil.

3. The method according to claim 1, wherein said particulate flavor agent is microencapsulated.

4. The method according to claim 2, wherein said microencapsulated flavor agent is a spray dried flavor agent.

5. The method according to claim 4, wherein said method further comprises extruding said gel floss and quenching said extruded gel floss.

6. The method according to claim 5, wherein said contacting occurs prior to said quenching.

7. The method according to claim 5, wherein said contacting occurs after said quenching.

8. The method according to claim 7, wherein said method further comprises softening at least the surface of said quenched gel floss.

9. A method according to claim 1, wherein said surface is rendered tacky by softening of said gel floss by heat.

10. A method according to claim 1, wherein said surface comprises a tacky formulation of a thermo-plastic elastomer material and an oil plasticizer.

11. The floss produced according to claim 1.

12. A gel floss comprising a surface to which is stably associated flavor particles.

13. The floss according to claim 12, wherein said flavor particles are adsorbed to said surface.

14. The floss according to claim 12, wherein said flavor particles are embedded in said surface.

15. The floss according to claim 12, wherein said gel floss comprises a core component encased in a gel component, wherein said gel component comprises a styrenic based resin in combination with an oil.

16. The floss according to claim 15, wherein said flavor particles are microencapsulated particles.

* * * * *